US007105058B1

(12) United States Patent
Sinyagin

(10) Patent No.: US 7,105,058 B1
(45) Date of Patent: Sep. 12, 2006

(54) APPARATUS FOR FORMING A MICROFIBER COATING

(75) Inventor: Dmitriy Sinyagin, San Carlos, CA (US)

(73) Assignee: PolyRemedy, Inc., Mountain View, CA (US)

( * ) Notice: Subject to any disclaimer, the term of this patent is extended or adjusted under 35 U.S.C. 154(b) by 169 days.

(21) Appl. No.: 10/382,422

(22) Filed: Mar. 5, 2003

Related U.S. Application Data

(60) Provisional application No. 60/362,175, filed on Mar. 5, 2002.

(51) Int. Cl.
*B05C 11/10* (2006.01)
*B05B 1/28* (2006.01)
*A61F 15/00* (2006.01)

(52) U.S. Cl. .......................... 118/713; 118/61; 118/62; 118/63; 118/629; 118/627; 239/291; 602/44; 602/45

(58) Field of Classification Search ................ 118/712, 118/713, 61–63, 308, 629, 627, 626; 427/2.31; 602/41–47; 239/290–301
See application file for complete search history.

(56) References Cited

U.S. PATENT DOCUMENTS

| | | | | |
|---|---|---|---|---|
| 4,869,936 | A * | 9/1989 | Moskowitz et al. | 427/455 |
| 5,520,735 | A * | 5/1996 | Mulder | 118/308 |
| 5,757,498 | A * | 5/1998 | Klein et al. | 356/630 |
| 6,520,425 | B1 * | 2/2003 | Reneker | 239/294 |
| 6,753,454 | B1 * | 6/2004 | Smith et al. | 602/41 |
| 2001/0003148 | A1 * | 6/2001 | Coffee | 602/42 |

* cited by examiner

*Primary Examiner*—George Koch
(74) *Attorney, Agent, or Firm*—MacPherson Kwok Chen & Heid LLP

(57) ABSTRACT

An apparatus and method for forming a microfiber coating includes directing a liquid solution toward a deposition surface. The apparatus includes a tube defining a volume through which the liquid solution travels. An electric field is applied between the origin of the liquid solution and the surface. A gas is injected into the tube to create a vortex flow within the tube. This vortex flow protects the deposition surface from entrainment of ambient air from the surrounding atmosphere.

27 Claims, 10 Drawing Sheets

APPARATUS FOR FORMING A MICROFIBER COATING

CROSS-REFERENCE TO RELATED APPLICATION

This application claims priority to U.S. provisional patent application No. 60/362,175 filed Mar. 5, 2002, the entire content of which is incorporated herein by this reference.

SCOPE OF THE INVENTION

The present invention relates to electro-hydrodynamic fiber forming, also commonly referred to as electro or electrostatic spinning. More specifically, it relates to using electro-hydrodynamic fiber forming to provide a mat of woven fibers.

BACKGROUND

Electro-hydrodynamic fiber forming generally involves the introduction of a liquid into an electrical field. The resulting electrical forces create a jet of liquid which carries an electrical charge. These liquid jets may be attracted to other electrically-charged objects at a suitable electric potential. As the jet of liquid travels, it elongates and it will harden and dry. The hardening and drying of the elongated jet of liquid may be caused by cooling of the liquid (e.g., where the liquid is normally a solid at room temperature), evaporation of a solvent by dehydration, (e.g., physically induced hardening), or by a curing mechanism (e.g., chemically induced hardening). The resulting fibers are collected on a suitably-located, oppositely-charged receiver and subsequently removed from it as needed, or directly applied to an oppositely-charged, generalized target area.

Various methods of electro-hydrodynamic fiber forming are known in the art. For example, U.S. Pat. Nos. 4,043,331 and 4,878,908 describe non-woven mats comprising a plurality of fibers of organic material produced by electrostatically spinning the fibers from a liquid including the material. The electro-hydrodynamic fiber forming technique may be used to form a dressing directly on a wound surface. The techniques known in the art, however, have several shortcomings, including failing to provide a consistent quality of microfibers and a sterile dressing.

Accordingly, there is a need in the art for a method and apparatus for forming a microfiber coating that provides consistent microfiber quality with safe and sterile operation.

SUMMARY OF THE INVENTION

The present invention, according to one embodiment, is a method for forming a fiber coating on a surface, from a supply of fiber-forming liquid having moisture, in an environment having an ambient pressure. The method includes the steps of applying an electrical potential between the supply and the surface to cause the fiber-forming liquid to travel from the source to the surface in a stream having a periphery and reducing the ambient pressure around the periphery of the stream to enhance removal of moisture from the stream so as to form a fiber coating of reduced moisture on the surface.

Another embodiment of the present invention is an apparatus for forming a microfiber coating on a surface. The apparatus includes a housing including a substantially cylindrical outer tube defining at least one internal volume, the tube having a first end and an outlet at a second end. A cartridge adapted to hold a fiber-forming mixture is coupled to the housing near the first end of the outer tube. A compressed gas source, having an inlet, is coupled to the housing for exchanging a gas with the internal volume. A power source is coupled to the housing to generate an electric field between the cartridge and the outlet.

Yet another embodiment is an apparatus for forming a microfiber coating on a surface. The apparatus includes a housing provided with an internal space and an opening. The housing has a port communicating with the internal space. A supply of a fiber-forming liquid is coupled to the port for introducing the fiber-forming liquid into the internal space. A voltage source is coupled to the housing for creating an electrical potential between the port and the surface so as to cause the fiber-forming liquid to travel from the port to the opening in a stream having a periphery. Means for reducing an ambient pressure around the periphery of the stream so as to remove moisture from the stream are coupled to the housing.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and description are to be regarded as illustrative in nature and not restrictive.

BRIEF DESCRIPTION OF THE DRAWINGS

The accompanying drawings, which are somewhat schematic in many instances and are incorporated in and form a part of this specification, illustrate exemplary embodiments of the invention and, together with the description, serve to explain the principles of the invention

DESCRIPTION OF THE INVENTION

Figure 1:
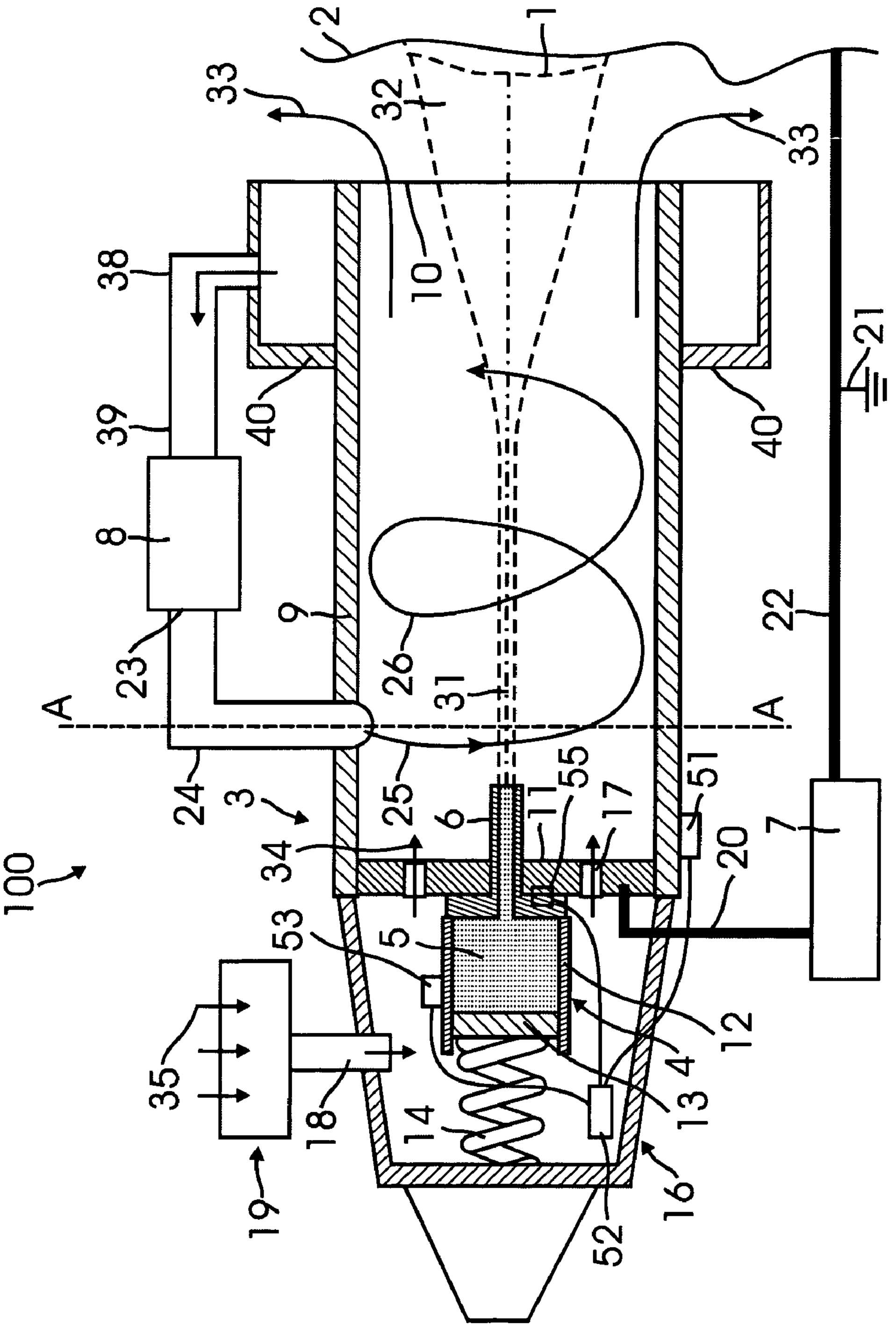
FIG. 1 is a schematic view of an apparatus for forming a coating, according to one embodiment of the present invention.

An apparatus 100 operates to form a microfiber coating 1 directly onto a deposition surface 2 (see FIGS. 1 and 2–10). The apparatus 100 uses electro-dynamical production of microfibers or micro-droplets from a polymer solution or sterile polymer mixture 5. In one embodiment of the present invention, the apparatus 100 is used to provide a sterile wound dressing and is sufficiently small to enable immediate use on a wounded patient before transport to a treatment facility.

The apparatus 100 includes a housing 3 ergonomically designed to be held in the hand of a medical provider, a cartridge 4, a battery (not shown), a high-voltage power source 7, and a micro-compressor 8 (or other known type of pressurized gas source). The cartridge 4, which is adapted to hole the sterile polymer mixture 5, includes a capillary 6 having an orifice at a distal end. The cartridge 4 may be designed as a disposable component or a refillable component. The housing 3 includes a cylinder or tube 9 defining an interior space, a cartridge support 11 including a port, in communication with the interior space of the tube 9, for receiving the capillary, a cartridge housing 16, and a gas collector 40.

The tube 9 has an opening or outlet 10 located at an end opposite the cartridge support 1. The tube 9 may be made of any material. In one embodiment the tube 9 is made from a non-conductive material, such as a plastic. In one embodiment, the length of the tube 9 is from about 5 cm to about 30 cm and the diameter is from about 1 cm to about 10 cm. An end of the tube 9 is connected to the cartridge support 11. The capillary 6 is located substantially along a longitudinal axis of the tube 9 and is directed toward the outlet 10. The orifice of the capillary 6 may be flush with the support 11 or protruding beyond a surface of the support 11. The further the capillary 6 extends into the tube 9, the stronger and less uniform an electrical field or potential applied to it becomes. The capillary 6 may be made from electro-conductive or semi-conductive material. In one embodiment, an internal diameter of the capillary 6 is from about 0.1 to about 3 mm, and a length is from about 1 to about 50 mm. In one embodiment, the capillary 6 extends from about 1 to about 10 internal diameters beyond the surface of the support 11. In another embodiment, more than one capillary 6 is connected to the cartridge 4. In one embodiment, the apparatus 100 includes more than one cartridge 4 connected to separate capillaries or to the same capillary 6.

The high-voltage power source 7 is connected to the capillary 6 by a wire 20 and to ground 21 or the surface 2 (or both) by a wire 22. Alternatively, the high-voltage power source 7 may be connected to the support 11, which is in electrical contact with the capillary 6. In this embodiment, the support 11 is made of electro-conductive or semi-conductive material. The high-voltage power source 7 provides controllable DC voltage in a range from about 5 kV to about 50 kV. The power source 7 may include a switch to turn the power it supplies on and off.

The cartridge 4 includes of one or more reservoirs 12. Every reservoir 12 is provided with at least one capillary 6. The reservoirs 12 may be stackable on top of each other or located side by side. The reservoir 12 may have equal or non-equal volumes and shapes. The reservoir 12 may be collapsible or syringe-type or any other type that allows delivery of the mixture 5 through the capillary 6 at a controlled rate. Any type of mechanical, electrical, magnetic, pneumatic, or hydraulic mechanisms may be used for pressurizing the mixture 5 in the reservoir 12 and directing the mixture 5 out the capillary 6 and into the tube 9. As an example, the cartridge 4 shown in FIG. 1 is a cylinder or syringe-type cartridge having a piston 13 that is driven into the reservoir 12 by a spring 14. The spring may be tensioned using a knob 15 to provide a controllable pressure to the piston 13. The delivery rate of the mixture 5 is determined by the force of the spring or pressurizing mechanism 14, the surface area and friction of the piston 13, hydraulic constrains of the capillary 6, and properties of the liquid mixture 5. In one embodiment, the mixture 5 is a solid material. In this embodiment, the apparatus 100 is provided with a heating and temperature controlled element (not shown) to melt the mixture 5 at least at the outlet of the capillary 6. In one embodiment, the pushing mechanism or piston 13 includes a latch or switch (not shown), controlled by an external signal or command from the user, to start or stop delivery of the mixture 5.

The cartridge 4 and the pressurizing mechanism or its components are enclosed by a cartridge cover or housing 16. All or part of the cover 16 is detachable from the housing 3 to provide access to the cartridge 4. Closing the cover 16 may initiate a mechanism to wind the pressurizing mechanism 14 for the cartridge 4. A gas conditioner 19 is coupled to the interior volume defined by the cover 16 by a gas inlet 18. The gas conditioner 19 may consist of one or more of a filter, a drier, a sterilizer, an odor, a chemical composition (like additions of ozone or ions), electrical conductivity, and a temperature controller. It may also consist of a fan if the flow constriction of the gas conditioner 19 is high. The direction of the fan may be controlled to create positive or negative pressure difference between the inside volume of the cover 16 and the ambient. In one embodiment, the gas conditioner 19 is directly connected to the inside volume of the tube 28 by a manifold, or pipes, or ducts, or other technique known in the art.

The support 11 may have through holes 17 that connect the internal volume of the tube 9 with the internal volume of the cover 16. In some embodiments, the holes 17 may be directed predominantly tangentially relative to the longitudinal axis of the tube 9 to create tangential rotation of the entering gas. In other embodiments, the holes 17 may be directly connected to the gas conditioner 19 through a manifold, pipes, or ducts.

Figure 3:
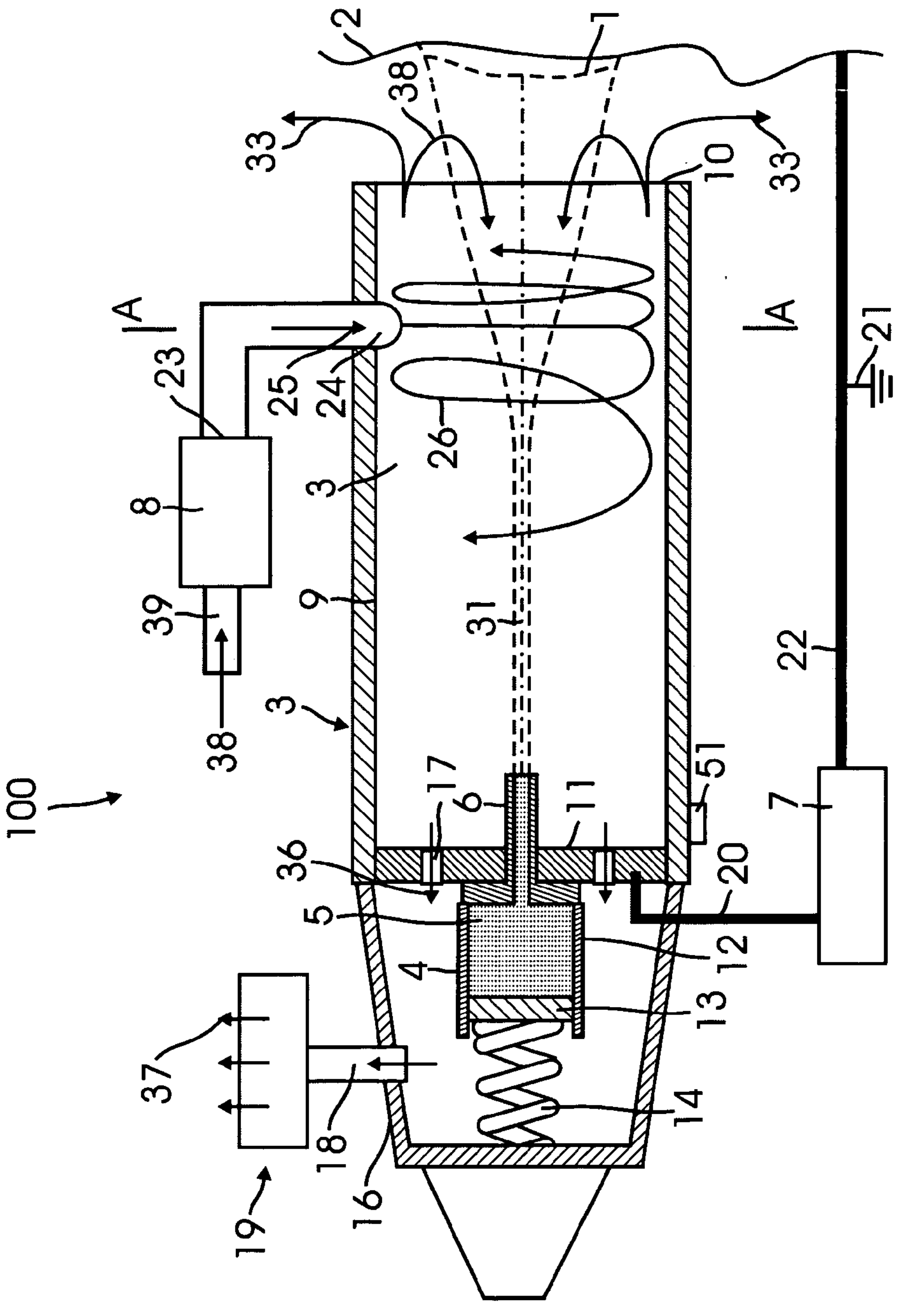
FIG. 3 is a schematic view of an apparatus for forming a coating, according to a second embodiment of the present invention, including a gas injection near an outlet of the apparatus.

The gas collector 40 surrounds the distal end of the tube 9 and is coupled to a compressor 8 by an inlet 39. The compressor 8 or other type of pressurized gas source may include a gas conditioner 19 such as a filter, a drier, a sterilizer, or components to control an odor, a chemical composition (like additions of ozone or ions), an electrical conductivity, or a temperature of the gas. The gas collector 40 operates to collect outgoing gas 33. A gas compressor outlet 23 is connected to a gas port or inlet 24 of the internal volume of the tube 9. The inlet 24 may be located close to the support 11 (as shown in FIG. 1) or close to the outlet 10 (as shown in FIG. 3) or there may be multiple and/or distributed inlets.

Figure 2:
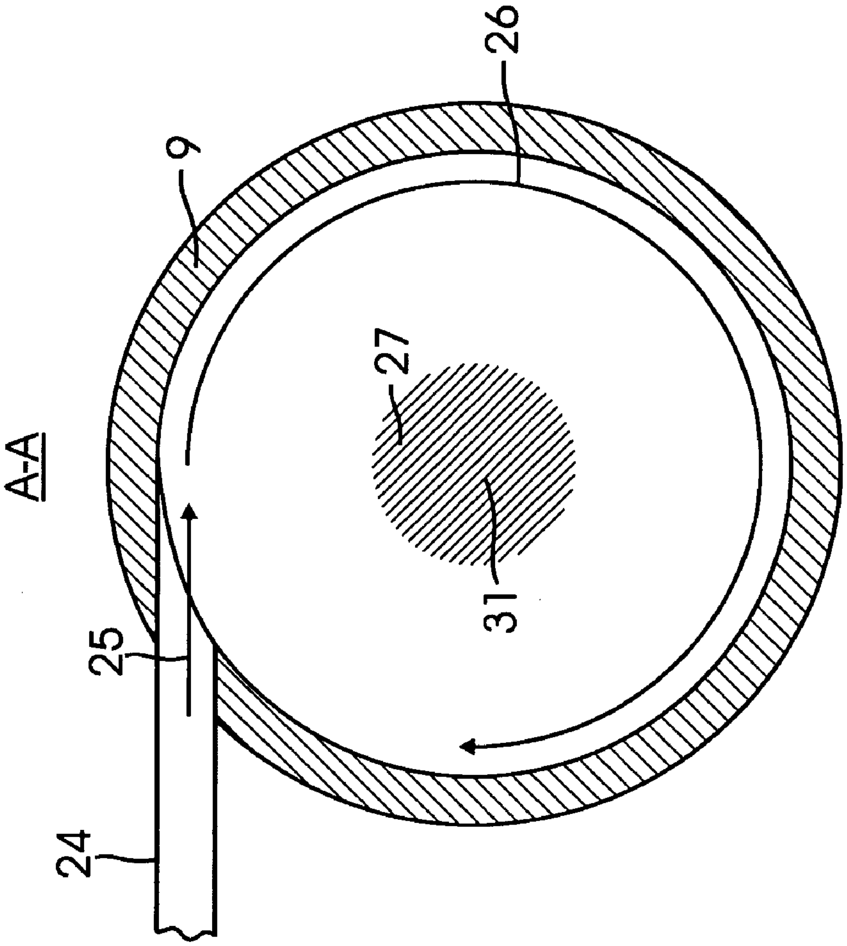
FIG. 2 is a sectional view taken along the line A—A in FIG. 1.

The inlet 24 may be directed tangentially relative to the longitudinal axis of the tube 9 (see FIG. 2). An injected gas 25 generates a vortex 26 inside the tube 9, which creates an area of reduced pressure in a central zone 27 (see FIG. 2) near a centerline or longitudinal axis of the tube 9. This reduced pressure in the central zone 27 is caused by the low pressure in the vortex 26 drawing gas away from the central zone 27. The velocity of the injected gas 25 in the vortex is maximal in the peripheral areas near the walls of the tube 9 and is almost zero in the central zone 27. The vortex effect is strongest in the cross-section of the tube 9 near the inlet 24. The strongest point of the vortex may be located about one tube 9 internal diameter distance upstream and downstream along the longitudinal axis. When the injected gas 25 exits the tube 9, through the outlet 10, it moves radially away from the tube 9 axis due to its tangential rotational momentum. As the injected gas 25 travels away from the inlet 24 toward the outlet 10, the velocity of the injected gas 25 decreases due to frictional forces between the injected gas 25 and the walls of the tube 9.

Figure 4:
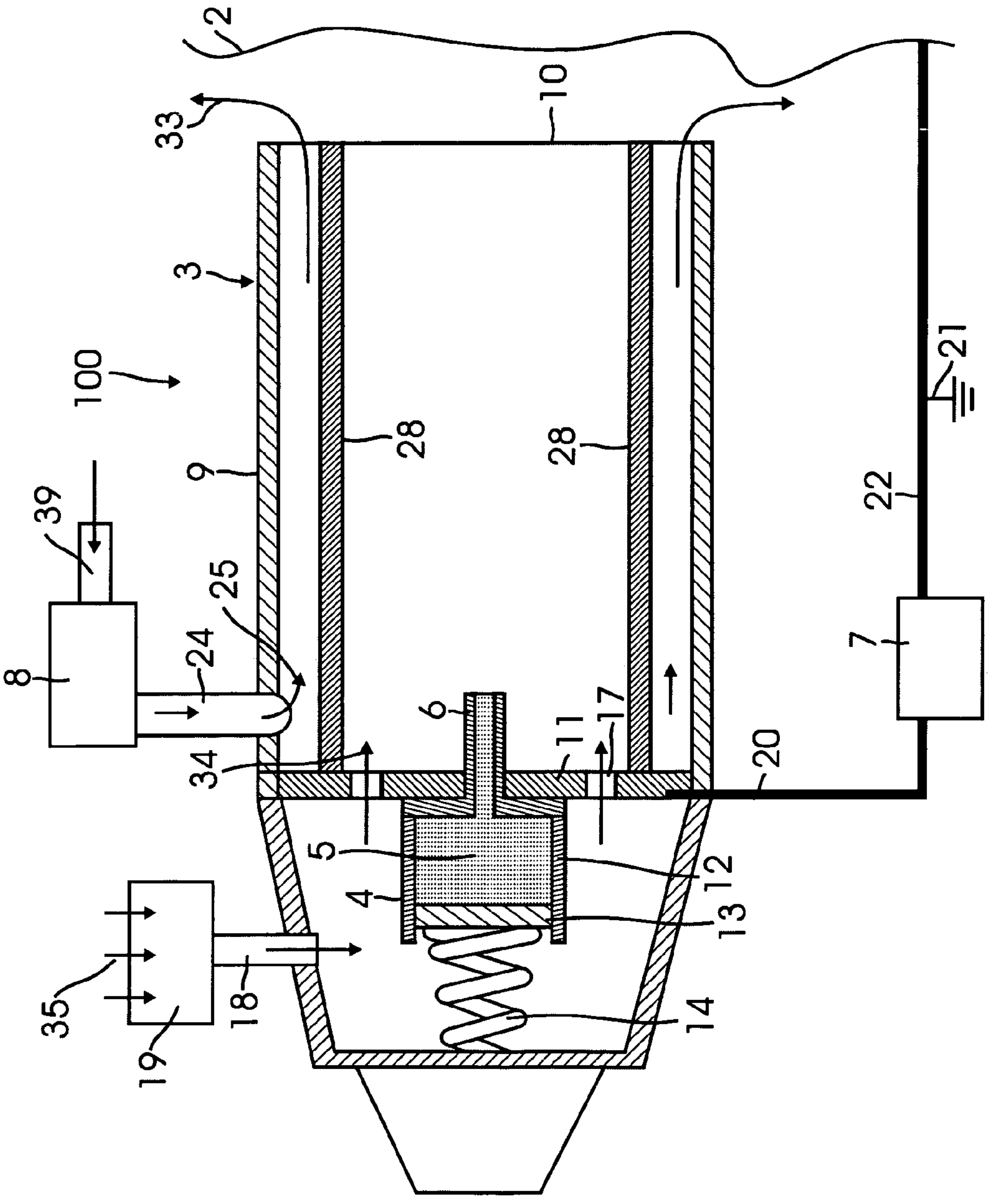
FIG. 4 is a schematic view of an apparatus for forming a coating, according to a third embodiment of the present invention, including a second tube disposed substantially coaxially with the outer tube.
Figure 5:
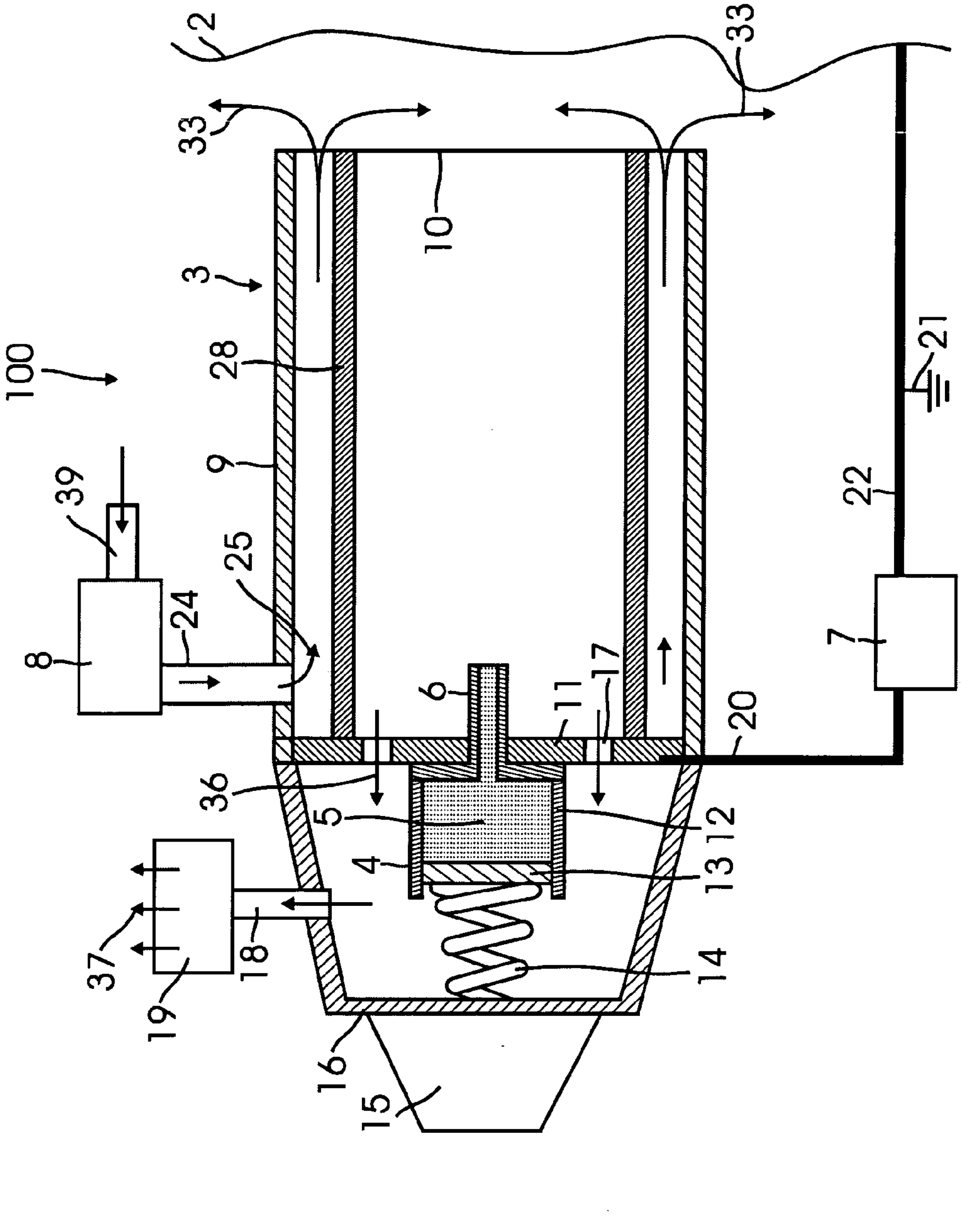
FIG. 5 is a schematic view of an apparatus for forming a coating, according to a fourth embodiment of the present invention, in which gas is non-tangentially injected between the tubes.

The apparatus 100 for non-contact forming of a microfiber coating 1 may be provided with second tube 28 that is located inside, and substantially coaxial with, the tube 9 (see FIG. 4). The tube 28 may be longer then tube 9 (see FIG. 6) or shorter (see FIG. 9). The distance between the outside surface of the tube 28 and the inside surface of the tube 9 may be varied and is in range from about 1 mm to about 40 mm. In the preferred embodiment, the distance between the tubes is less near the outlet 10 than the distance between the tubes near the support 11. A first end of the tube 28, located near the outlet 10, is open. A second end of the tube 28 is hermetically closed so as to prevent the injected gas 25 from reaching the interior volume of the tube 28. The holes 17 in the support 11 are positioned to provide a gas connection between the inside volume of the cover 16 and the inside volume of the tube 28. The tube 28 may be made with side through holes 29 that may be any shape (see FIG. 7). The tube 28 may be made, in whole or in part, from open-cell porous material. The holes 29 or porosity of the tube 28 provide controllable gas penetration from inside volume of the tube 28 into the volume between the tube 28 and the tube 9.

Figure 9:
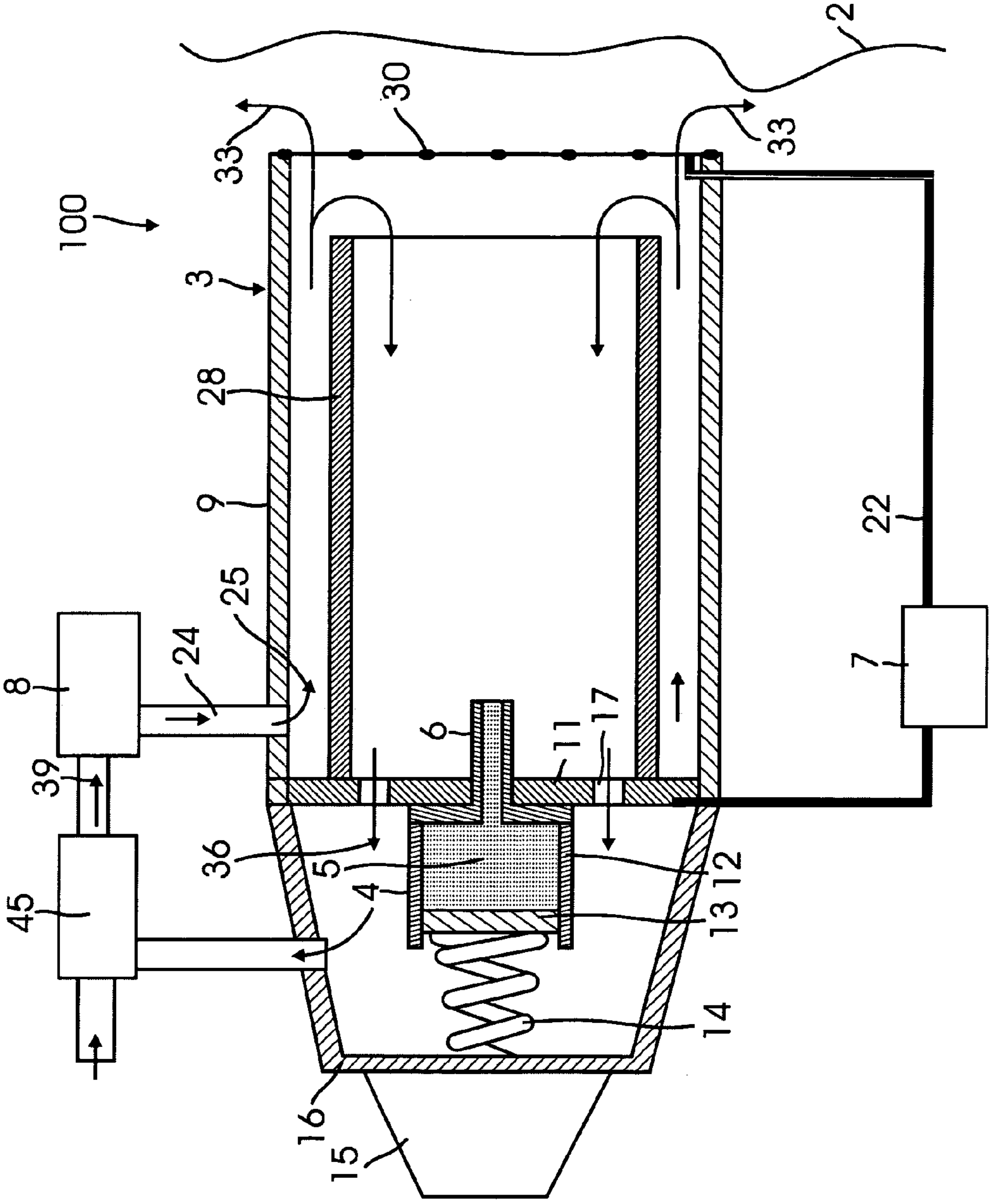
FIG. 9 is a schematic view of an apparatus for forming a coating, according to an eighth embodiment of the present invention, including a second electrode near the outlet and further including a second coaxially-disposed tube.

In one embodiment, the outlet 10 is provided with a second electrode 30 connected to the high voltage power source 7 with an electric polarity that is opposite to that connected to the capillary 6 (see FIG. 9). The second electrode 30 is oriented generally perpendicular to the longitudinal axis of the tubes 9 and 28, an may include openings or wire mesh to create minimal resistance to gas flow through the outlet 10 (see FIG. 10).

In one embodiment, the apparatus 100 includes a distance sensor 51 adapted to measure a distance between a distal end of the capillary 6 and the surface 2. Because the location of the capillary 6 relative to other components is fixed, the sensor may be install at any convenient location to measure the distance between the surface 2 and any predetermined reference point on the apparatus 100. The distance sensor 51 may, for example, be an ultrasonic sensor, sold as model RPS-409A-80, by Migatron, Inc., or a laser displacement sensors, sold as model LK501, by Keyence, Inc.

The sensor generates a signal representing the distance to the surface 2 and provides the signal to a microcontroller or control circuit 52. Based on this signal, the control circuit 52 calculates the distance between the distal end of the capillary 6 and the surface 2 and provides several functions. The control circuit 52 may function to turn the power source 7 on or off and to activate the pressurizing mechanism as needed. The control circuit 52 may function to decrease or increase the voltage delivered by the power source 7, based on the distance. The control circuit 52 may provide an indication to the user to correct the distance between the apparatus 100 and the surface 2 by using, for example, an audio or visual signal (or both).

The cartridge 4 may include a cartridge sensor 53 for generating a signal representative of the amount of mixture 5 remaining in the cartridge 4. The cartridge sensor 53 may provide a signal to the control circuit 52, which may inform the user of the amount of mixture 5 left in the cartridge 4 and may indicate when the cartridge 4 has to be replaced. The control circuit 52 may also turn off the power source 7 and the pressurizing mechanism, based on the signal from the cartridge sensor 53. The cartridge sensor 53 may be any type of sensor known in the art.

In one embodiment, the cartridge 4 includes a key element 55 adapted to prevent use of a cartridge without the key, prevent operation of the apparatus 100 if the cartridge 4 is installed incorrectly, and determine the type of the cartridge 4, which in turn indicates the type of mixture 5 and the reservoir volume. The key element 55 may include a sensor adapted to provide information to the control circuit 52 to control the power source 7 or the pressurizing mechanism parameters (or both). Any key element 55 known in the art may be used, including mechanical, electrical, magnetic, and optical key elements.

The housing 3 is design to meet the ergonomic requirements for convenient handling. The housing 3 may be provided with at least one handle or a separate case (or both). All components of the apparatus 100 may be placed inside the housing 3, or some of the components (e.g., battery, air compressor, or filters) may be placed inside the separate case and be connected to the apparatus 100 with wires or tubes. The housing 3, tube 9, second tube 28 and gas collector 40 may be made from transparent material to allow the user to see the surface 2 and facilitate positioning and targeting and to monitor visually the deposition of the microfibers and the coating 1 formed on the surface 2.

During operation of the apparatus 100, the cartridge 4, which is filled with a solid material or liquid mixture 5, is installed on the support 11 such that the capillary 6 protrudes through an opening in the support 11 and into the tube 9 (see FIG. 1). The cover 16 is closed and the knob 15 is turned to increase the pressure in the pressurizing mechanism 14. If present, the cartridge sensor 53 and the control circuit 52 indicate that the cartridge 4 is full. If present, the cartridge key element 55 provide a signal to the control circuit 52 confirming that the cartridge 4 is installed correctly and indicating the cartridge 4 or mixture 5 or solid material type. The control circuit 52 sets the voltage delivered by the power source 7, based on the predetermined cartridge type.

The user positions the apparatus 100 generally perpendicular to the surface 2 at a distance of from about 0.5 to about 5 cm between the outlet 10 and the surface 2. If present, the distance sensor 51 provides a signal to the control circuit 52 indicative of the distance between the sensor and the surface 2, and the control circuit 52 determines whether the apparatus 100 is located at an allowable distance from the surface 2. If the distance is out of the range, the indicator informs the user with an audio or visual signal to prompt the user to correct the distance.

The user turns on the apparatus 100, which activates the power source 7 and the pressurizing mechanism 14. The mixture 5 is pushed out of the capillary 6 at a rate of from about 0.05 to about 5 mL per minute and directed into the tube 9. The mixture 5 may be pushed out at rate of from about 0.5 to 3 mL per minute. The mixture 5 exits the distal end of the capillary 6 and is directed through the tube 9 as a stream or liquid jet 31 having a periphery. At the distal end of the capillary 6, the periphery of the stream of liquid jet 31 is substantially within the central zone 27 and, as the stream of liquid jet 31 travels longitudinally toward the outlet 10, it expands to a diameter of the fiber forming zone 32 (see FIG. 1). Because the capillary 6 is charged to a high voltage potential, by the power source 7, the liquid jet 31 is charged with a corresponding potential. The electrical potential or electrostatic field is applied between the capillary 6 and the surface 2. The forces caused by the electrostatic field and the surface tension cause acceleration of the liquid jet 31, which thins and, at some distance from the capillary 6, transforms to an expanding flow of charged microfibers moving along the longitudinal axis of the housing 3. These microfibers then exit through the outlet 10 and enter an intermediate space or microfiber formation zone 32. By the time the microfibers reach the surface 2 they are dry and have an average diameter of less than 100 micron. In one embodiment, the microfibers, at the surface 2, have an average diameter of less than 1 micron. In another embodiment, the microfibers, at the surface 2, have an average diameter of from about 0.1 to about 10 microns. The microfibers then randomly attach to the surface 2 thereby forming a non-woven microfiber coating 1. The apparatus 100 is configured to adjust gas pressure in the tube 9 to create a flow of gas through the tube. In some embodiments, the gas pressure is increase and, in other embodiments, the gas pressure is decreased with respect to an ambient pressure.

To accomplish wound dressing, the user positions the outlet 10 near a wound surface of a patient and activates the apparatus 100, which results in covering the wound with a coating 1 of microfibers deposited painlessly and directly onto the wound. The user can determine the size, thickness, and shape of the coating 1 by the time and location of activation of the apparatus 100. The coating 1 conforms to the three-dimensional topography of the wound, thereby providing better protection to the wound and enabling more direct and complete delivery of any medically important additives, which are incorporated in the dressing, to the wound. The accelerated flow of the microfibers allows greater penetration of the fibers into deep wounds such as lacerations, and therefore, improved protection of the wound and delivery of pharmaceutical or therapeutic agents. The microfiber size and layer thickness, polymer type, and additives determine the properties of the resulting wound dressing.

The user moves the apparatus 100 over the surface 2 maintaining a generally constant distance between the outlet 10 and surface 2. In one embodiment, the distance sensor 51 continuously tracks this distance and provides a signal to the control circuit 52, which may signal the power source 7 to increase the voltage if the distance increases or reduce the voltage proportionally if the distance decreases. In one embodiment, the voltage of the power source 7 is increased more than proportionally to increase the velocity of the microfibers to maintain a constant diameter. If the distance is outside of acceptable range, the control circuit 52 may turn off the power source 7 and the pressurizing mechanism 14. Adjusting the voltage applied by the power source 7 ensures quality and repeatability of the properties of the microfibers. The signal from the distance sensor 51 is also used by the control circuit 52 to provide an audio or visual indication to notify the user when the distance is outside of a predetermined optimal operating range, which helps the user to prevent touching the wound surface by the apparatus 100, and greatly simplifies the use of the apparatus 100. In one embodiment, the pressure on the cartridge 4 is also adjusted in response to a signal from the distance sensor 51.

Figure 10:
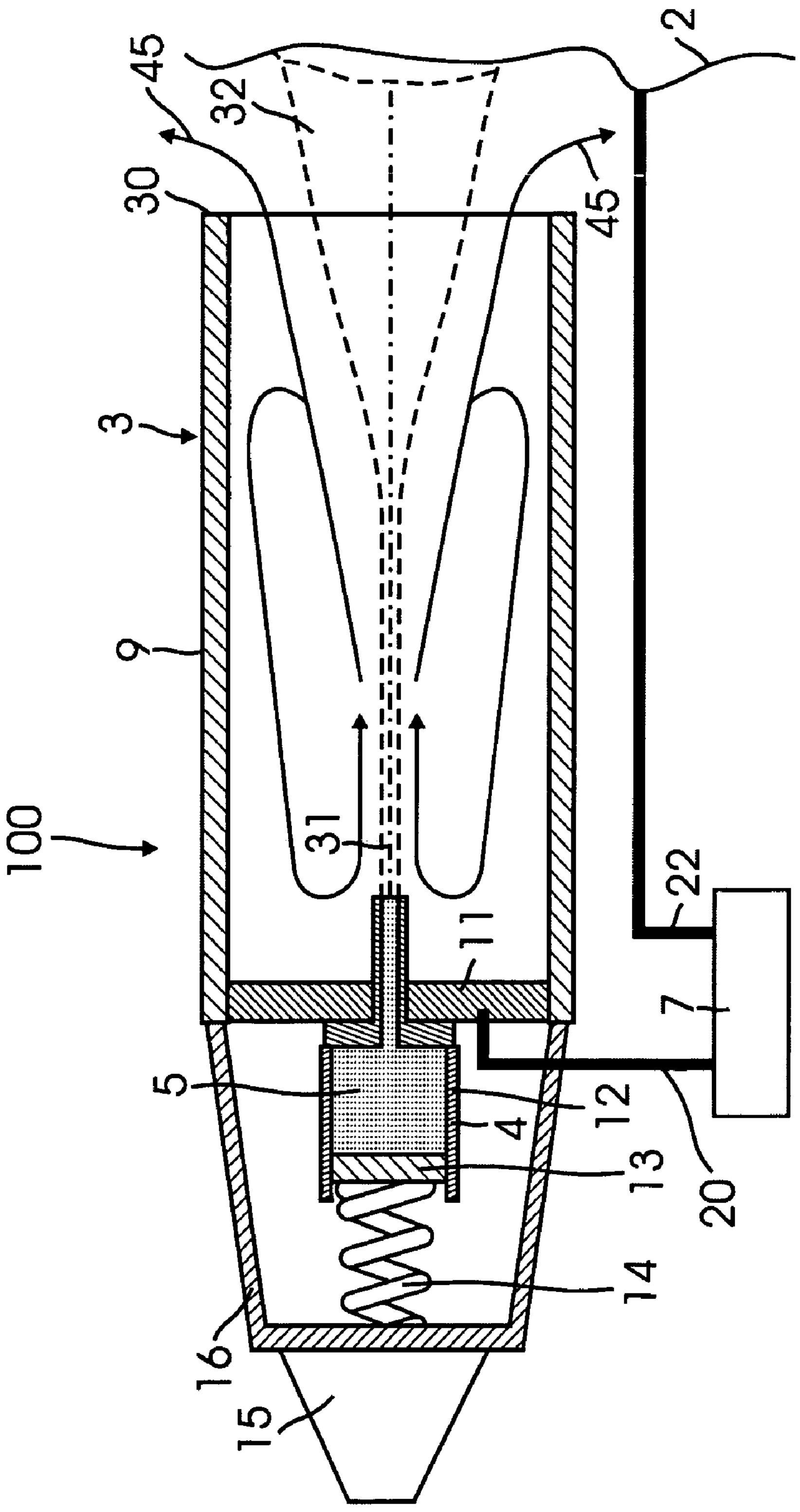
FIG. 10 is a schematic view of an apparatus for forming a coating, according to a ninth embodiment of the present invention, in which the tube narrows near the outlet.

In one embodiment, the cross-sectional dimension of the tube 9 is chosen such that the diameter of the outlet 10 is slightly larger than the diameter of the microfiber formation zone 32 (see FIG. 10). The diameter of the outlet 10, for example, may be from about 5 to about 20 mm larger than the diameter of the zone 32. The liquid jet 31, accelerated in the electrostatic field, may have a velocity of from about 1 to about 20 meters per second depending on the liquid flow rate, diameter of the capillary 6, and a value of the electrostatic field. The liquid flow creates strong surrounding gas entrainment or outgoing gas 33, 45 out of the tube 9, which creates reduced pressure around the liquid jet 31, because the ambient air does not penetrate into the tube 9 due to narrow gap between the liquid jet 31 and internal wall of the tube 9. During drying of the liquid jet 31, while flying from the capillary 6 to the surface 2, solvent evaporates from the liquid jet 31 and enters the central zone 27, which creates a flow of solvent vapor that may reach several liters per minute depending on the flow rate of the liquid jet 31 and the solvent concentration and volatility in the liquid. This vapor flow replaces air inside the tube 9. The solvent vapor recirculates inside the tube 9 and provides sterile and repeatable conditions for fiber forming and electrical discharge, which is not dependent on the cleanliness and humidity of the ambient air.

The air compressor 8, or any known type of pressurized gas source, delivers a preconditioned air into the tube 9 at a volumetric flow rate of from about 1 to about 100 liters per minute. The increased pressure inside the tube 9 prevents penetration of the ambient air into the tube 9 and keeps the conditions for the electric discharge, and formation of microfibers from the liquid jet 31, repeatable and independent of ambient air characteristics. The increased pressure inside the tube 9 also prevents penetration of dust or aerosols into the tube 9, which helps to keep the liquid jet 31, the microfiber coating 1, and the covered surface 2 sterile, which prevents contamination of the wound. The injected gas 25 into the tube 9 also reduces the probability of contact of the apparatus 100 with the surface 2. If the user positions the outlet 10 close to the surface 2, the outgoing gas 33 exiting the outlet 10 creates a force that pushes the apparatus 100 away from the surface 2.

As described above, in some embodiments, the inlet 24 is oriented tangentially to the longitudinal axis of the tube 9, which generates a vortex 26 and a low-pressure central zone 27 (see FIG. 2). The velocity of the air in the central zone is close to zero, thus it does not disturb flow of the liquid jet 31 from the capillary 6 toward the outlet 10. This lower than ambient pressure accelerates the evaporation of the solvent from the liquid jet. Due to the centrifugal force provided by the vortex 26, the flow of the expanding solvent vapor is radial from the liquid jet 31, which reduces the partial vapor pressure surrounding the liquid jet 31 and further intensifies the evaporation of solvent from the liquid jet 31. The rotating, outgoing gas 33 exits the outlet 10 in a circular motion with the axis of rotation generally coinciding with the longitudinal axis of the tube 9. The outgoing gas 33 has a radial velocity component due to tangential rotation in the tube 9. The outgoing gas 33 is moving along the surface 2 radially away from the apparatus 100 with little impingement upon the surface 2, while protecting the microfiber deposition zone from penetration of the ambient, non-conditioned air. In the microfiber deposition zone, the longitudinal and radial velocity components of the outgoing gas 33 exiting from the outlet 10 are close to zero, which prevents disturbing formation of the coating 1 on the surface 2.

The injected gas 25 may be preconditioned as required for optimal operation, protection of the microfiber polymer and wound surface, and to ensure reproducible conditions for the electrostatic field. This pre-conditioning may include, for example, ensuring that the injected gas 25 is clean and sterile, controlling the temperature and humidity, and specifying the chemical composition (e.g., inert, non-oxidizing, oxidizing, or ozone rich).

If the support 11 is provided with holes 17, an additional, supplemental gas 34 may be delivered into the tube 9 to further reduce pressure in the central zone 27 of the vortex 26 relative to the ambient air pressure. Like the injected gas 25, the supplemental gas 34 may be preconditioned to support optimal operation. This preconditioning, performed by the gas conditioner 19, may include, for example, ensuring that the supplemental gas 34 is clean and sterile, controlling the temperature and humidity, and specifying the chemical composition (e.g., inert, non-oxidizing, oxidizing, or ozone rich). The gas conditioner 19 may include a fan to pump the ambient gas 35 into the cover 16 or directly to the holes 17, to assist in overcoming the hydrodynamic constrains (e.g., pressure drops) associated with the conditioning elements (e.g., filters and absorbers). Alternatively, the supplemental gas 34 may be drawn into the tube 9 by the low-pressure zone 27.

Delivery of two gases 25, 34 into the tube 9 allows conditioning of each gas according to different parameters. For example, the injected gas 25 is often delivered at a higher flow rate than the supplemental gas 34. The injected gas 25 may be clean ambient air, while the supplemental gas 34 is sterile, dry air. The properties of the supplemental gas 34, that is drawn into the low-pressure zone 27 of the vortex 26, mainly determines the conditions of the electrical discharge and flow of the liquid jet 31. At the same time, because of the very low flow rate of the supplemental gas 34, it does not disturb the flow of the liquid jet 31 or the resulting microfibers to the surface 2 or forming of the coating 1 on the surface 2.

In some embodiments, inlet 24 is located close to the outlet 10 (see FIG. 3). In this case, the outgoing gas 33 exiting the outlet 10 provides the same protection from the ambient air without disturbing the liquid jet 31, microfiber formation zone 32 and the microfiber coating 1. If the injected gas 25 is injected into the tube 9 tangentially, the vortex effect and reduced gas pressure in the central zone 27 may cause reverse-flow gas 36 generally along the longitudinal axis of the tube 9 toward the support 11. This reverse-flow gas 36 may be pumped out of the tube 9, through the holes 17 and the cover 16, by the a pump in the gas conditioner 19. The reverse-flow gas 36 may draw in back-flow gas 38 from near the surface 2, which transports the solvent vapor from the microfiber formation zone 32 back into the tube 9. The reverse-flow gas 36 may also carry the solvent vapor that evaporates from the liquid jet 31. The solvent vapor is then removed by the reverse-flow gas 36 and, if present, the pump or fan located in the gas conditioner 19, which results in a reduction of the solvent vapor carried by the outgoing gas flow 33 to the ambient atmosphere.

The pump may include elements to utilize, destroy, absorb, or deodorize the solvent vapor, so that to release a clean gas 37 to the ambient atmosphere. The outlet of the gas conditioner 19 may be connected to the inlet 39 of the compressor 8 so as to recycle the injected gas 25 by adding it to the pressurized gas source or by mixing it with ambient air in the inlet 39 of the compressor 8. This recirculation may extend the lifetime or reduce the load on (and size of) gas conditioning elements of the compressor 8. Removal of the solvent vapors from the tube 9 with the reverse-flow gas 36 reduces the release of the solvent vapors to the ambient atmosphere with the outgoing gas 33, which improves user operating conditions and reduces risk of exposure to the solvent vapors. It also allows for an increase in the throughput of the apparatus 100, because increasing the liquid jet 31 flow rate will not result in a corresponding increase in the solvent vapor emission from the apparatus 100.

In one embodiment, the inlet 39 of the compressor 8 is connected to the gas collector 40 that surrounds the outlet 10 (as shown in FIG. 1). In this embodiment, a substantial portion of the outgoing gas 33 is returned back to the compressor 8 and re-injected into the tube 9, which allows a further reduction in the amount of solvent vapor released to the ambient atmosphere. Additionally, gas recirculation reduces the load on the gas conditioning elements of the compressor 8 and extends their lifetime.

In the embodiments where the apparatus 100 includes a second tube 28 disposed within the tube 9 (see FIGS. 4–7 and 9), the injected gas 25 is delivered between the tubes 9 and 28. In these embodiments, the humidity and temperature of the injected gas 25 may be not preconditioned, because this gas does not interact with the liquid get 31 and, thus, does not affect the electric discharge between the capillary 6 and surface 2. If the injected gas 25 is injected tangentially between the tubes 9 and 28 (see FIG. 4), it escapes the outlet 10 radially, due to its centrifugal inertia, and does not impinge forcefully upon the surface 2 or disturb the coating 1. The outgoing gas 33 prevents penetration of outside air into the formation zone 32 and into the apparatus 100. Likewise, the vortex effect creates reduced pressure inside the tube 9. This reduced pressure increases the rate of solvent evaporation and polymer drying in the liquid jet 31. The reduced pressure inside the tube 28 also allows an additional preconditioned, supplemental gas 34 to be drawn into the tube 28 through the filters located in the gas conditioner 19. This flow of dry gas displaces the solvent vapors from the tube 28, which provides repeatable conditions for electrical discharge and accelerates drying of the liquid jet. The solvent vapors are removed from the apparatus 100 together with the flow of outgoing gas 33, which includes the supplemental gas 34. In these embodiments, a gas collector 40 may also be used, as described above, to collect a portion of the outgoing gas 33.

If the injected gas 25 is delivered non-tangentially between the tubes 9 and 28 (see FIG. 5), it impinges upon the surface 2 and creates increased pressure inside the tube 28. This increased pressure, creates a back flow condition that carries the solvent vapors 36 out of the internal volume of the tube 28 through the holes 17 and gas conditioner 19, where the solvent vapors are removed or destroyed before the gas is released to the ambient atmosphere. The tube 28 may be shorter that the tube 9 (see FIG. 9). This configuration reduces the velocity of the gas impinging upon the surface 2 and improves displacement of the solvent vapors 36 from the internal volume of the tube 28.

Figure 6:
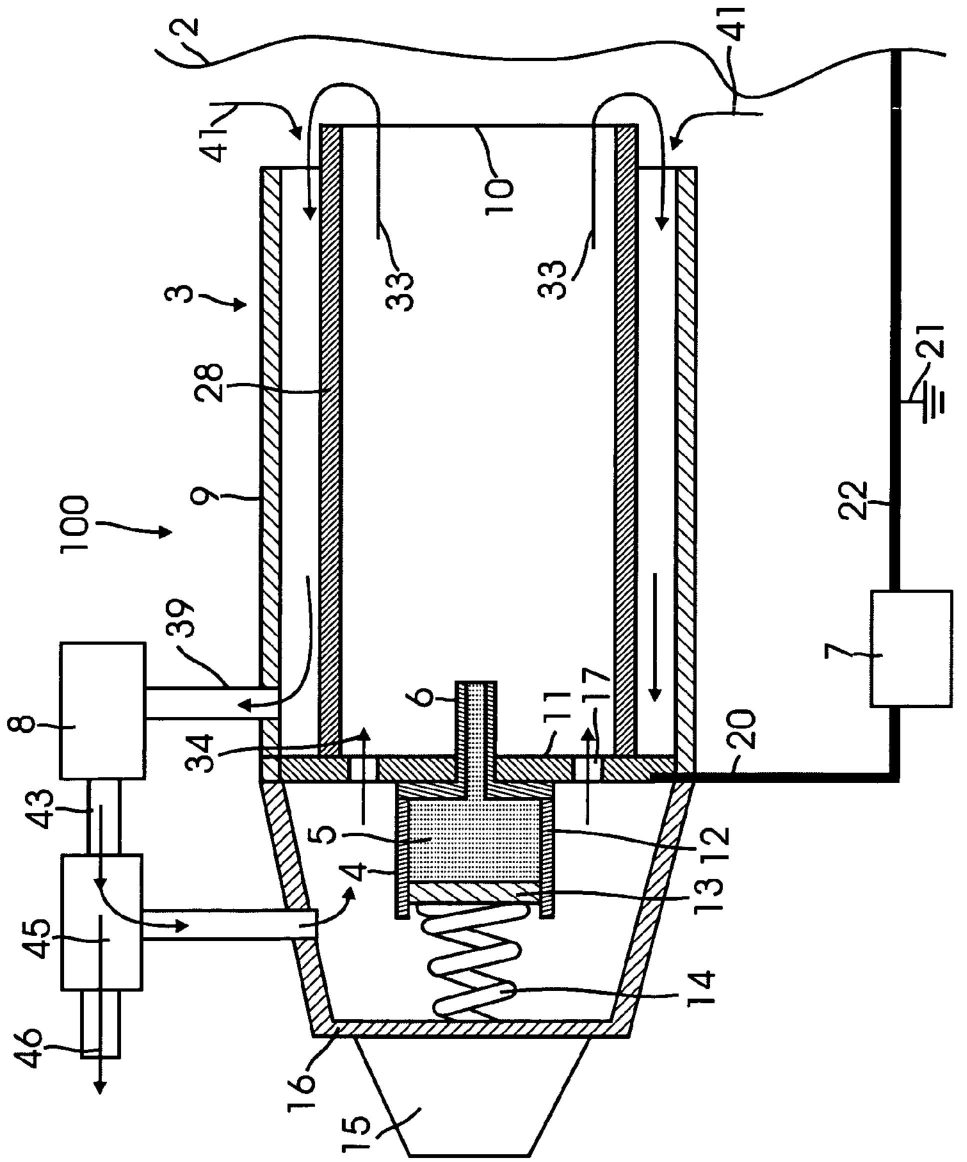
FIG. 6 is a schematic view of an apparatus for forming a coating, according to a fifth embodiment of the present invention, in which gas is drawn from the volume between the tubes.

In one embodiment, the inlet 39 of the compressor 8 is connected to the tube 9 near the location of the support 11 (see FIG. 6). In this embodiment, the compressor 8 pumps the collected gas 38 from the volume between the tube 9 and tube 28. The collected gas 38 is a combination of outgoing gas 33 exiting the outlet 10 and ambient air 41 from the periphery of the tube 9. This pumping action creates an area of reduced pressure near the outlet 10 and inside the tube 28. The draw of gas into the area between the tube 9 and the tube 28 prevents the ambient air 41 from entering the microfiber formation zone 32 and the space between the tubes 9 and 28, which prevents possible contamination affecting the electrical discharge. The outgoing gas 33, carrying the solvent vapor, exits the internal volume of the tube 28 through the outlet 10 and, at least a portion, is drawn into the volume between the tubes 28 and 9, which prevents escape of the solvent vapor to the ambient atmosphere. The tube 28 may be made longer than the tube 9 to prevent a "suction cup" effect when the outlet 10 is brought close to the surface 2. The tube 28 may be from about 1 to about 20 mm longer than the tube 9. The outlet 43 of the compressor 8 may be connected to a conditioning unit 45, which removes the solvent vapor such that harmless gases 46 are released to the ambient atmosphere.

The reduced pressure inside the tube 28 may be used to draw a preconditioned, supplemental gas 34 into the tube 28. This preconditioned (e.g., controlled humidity, temperature, cleanness, or sterility) supplemental gas 34 may be conditioned by the conditioning unit 45. The supplemental gas 34 may be drawn from the collected gas 38. This flow of supplemental gas 34 is small to prevent impingement on the surface 2 and disturbance of the microfiber forming zone and coating 1. In one embodiment, this flow is from about 2 to about 20 liters per minute and is enough to displace the solvent vapors from the tube 28, which provides repeatable conditions for the electrical discharge and accelerates drying of the liquid jet.

Figure 7:
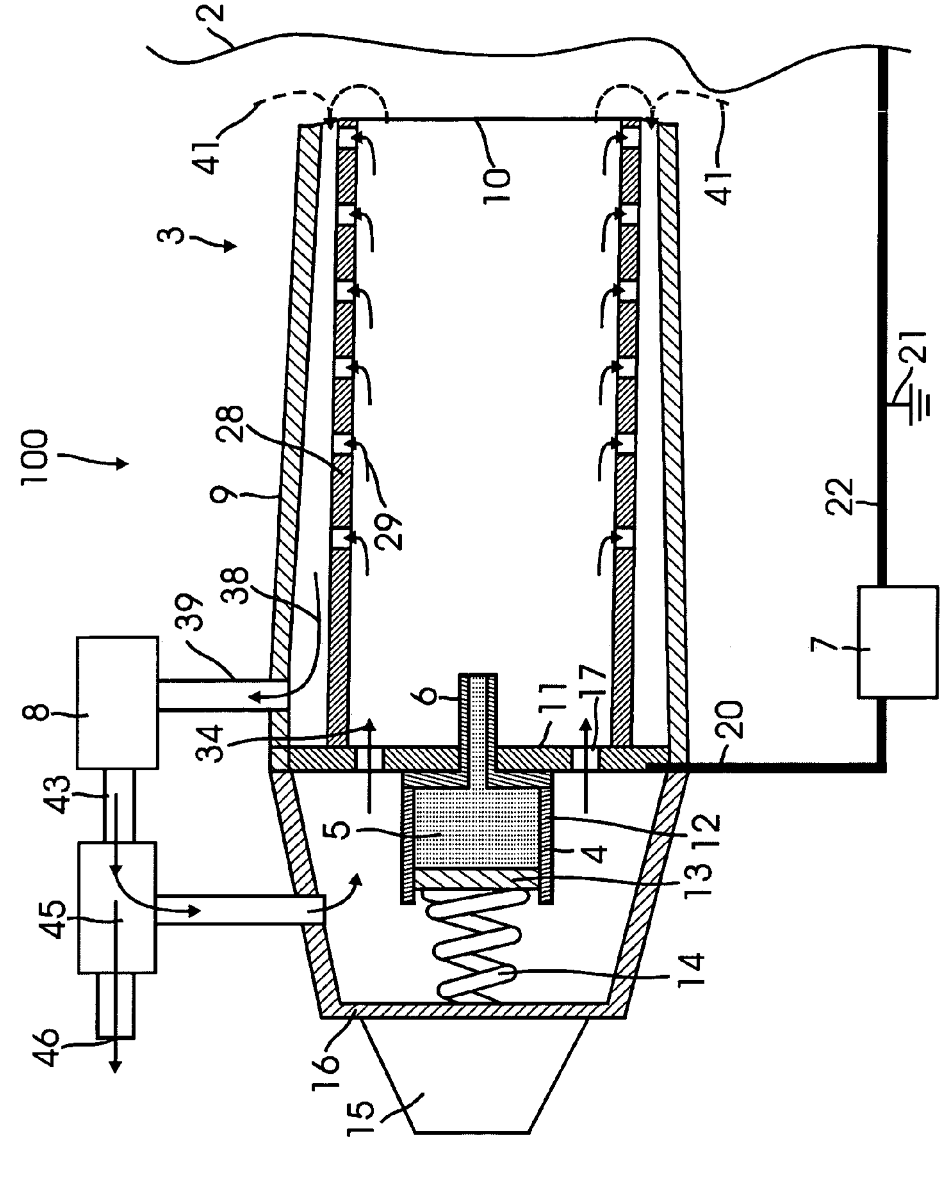
FIG. 7 is a schematic view of an apparatus for forming a coating, according to a sixth embodiment of the present invention, in which the inner tube is porous.

In one embodiment, the tube 28 is permeable (e.g., porous, perforated, or slotted), which allows the solvent vapors and outgoing gas 33 inside the tube 28 to flow radially and escape through the permeable wall of the tube 28 (see FIG. 7). This prevents significant flow near the surface 2 and disturbance of the coating 1. In this embodiment, the compressor 8 draws air from the space between the tube 9 and the tube 28, which creates a pressure lower than the ambient pressure. The pressure gradually increases along the length of the tube 28 (in accordance with the gas permeability of tube 28) so as to be close to the ambient pressure near the outlet 10. The flow of ambient air 41 into the inlet 39 of the compressor 8 is thus minimized, which reduces capacity requirements for the gas conditioning elements. In other words, the collected gas 38 is primarily gas drawn from inside the tube 28. The reduced pressure inside the tube causes the flow of a supplemental gas 34 into the tube 28 through the holes 17. The supplemental gas 34 may be conditioned collected gas 38, as described above.

The apparatus 100 may include more tubes disposed substantially concentric with the tube 9. The pressure between the neighbor tubes may be set higher or lower than ambient pressure. Correspondingly, the gas flows are directed in or out relative to the internal volumes between the neighbor tubes. This configuration allows protection of the coating formation zone 32, and the electrical discharge zone, from the ambient air, and prevents effluent or emission of potentially hazardous, volatile components from the coating 1.

Figure 8:
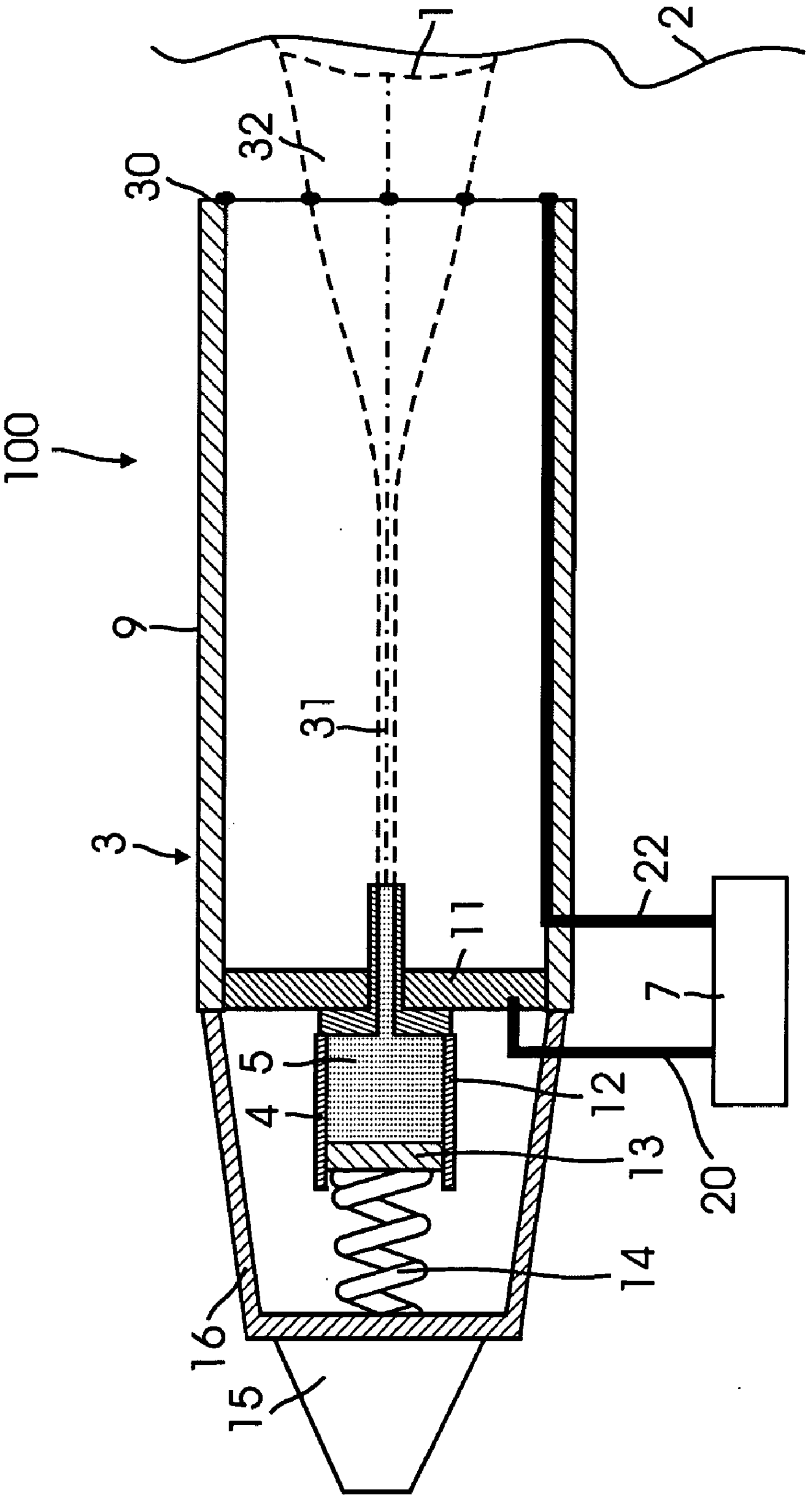
FIG. 8 is a schematic view of an apparatus for forming a coating, according to a seventh embodiment of the present invention, including a second electrode located near the outlet.

In one embodiment, the apparatus 100 is provided with at least one additional electrode 30 (see FIGS. 8 and 9). The electrode 30 is made with high degree (e.g., greater than 60%) of open area such that it does not significantly affect gas flow for the configurations described above. The use of the second electrode allows using the high voltage power source 7 with a voltage output that is floating or isolated from ground and without connection to the surface 2, which allows for an increase of electrical current because of the surface 2 (e.g., a portion of the human body) is no longer a part of the electrical circuitry. Increasing the electrical current enables an increase in the flow rate of the liquid and, correspondingly, the throughput of the apparatus 100. The electrical field between the capillary 6 and the second electrode 30 (1–10 kV/cm) accelerates the liquid 31, thins and transform it into microfibers or droplets, depending on the electrical field strength and fiber-forming properties of the mixture 5. In one embodiment, electrical field is between about 1 kV and about 10 kV per cm. The flow of the fibers or droplets, accelerated by the electrical field, may reach from between about 10 and about 50 meters per second. Part of the fibers or droplets may stick to the second electrode 30, but a significant part of fibers or droplets penetrate through the openings of the second electrode 30, and are deposited onto the surface 2 forming the coating 1.

The electrode 30 may also be connected to the surface 2. The electrode 30 may be placed under either positive or negative potential relative to the surface 2 (or each other), which may be achieved by connecting the electrode 30 and the surface 2 to an additional power supply, or interconnecting them with corresponding resistors having a value of from about 0.1 to 100 M Ohm, which causes the corresponding difference of the potentials between the connection points.

The cartridges 4 are filled with a desired polymers and additives mixed at its place of manufacture in sterile conditions and hermetically sealed for long storage. The volume of the mixture 5 is sufficient for one patient treatment. The cartridges 4 may be filled with a substantially homogeneous mixture 5 of any of a variety of hydrophilic and at least weakly hydrophobic polymers that may optionally be blended with any of a number of medically important wound treatments, including analgesics and other pharmaceutical or therapeutic additives. Such polymeric materials suitable for forming microfibers may include, for example, those inert polymeric substances that are absorbable or biodegradable (or both), and that react well with selected organic or aqueous solvents, or that dry quickly. Essentially any organic or aqueous soluble polymer or any dispersions of such polymer with a soluble or insoluble additive suitable for topical therapeutic treatment of a wound or for skin treatment or protection may be employed.

Examples of suitable hydrophilic polymers include, but are not limited to, linear poly(ethylenimine), cellulose acetate and other grafted celluloses, poly (hydroxyethylmethacrylate), poly (ethylene oxide), and poly vinylpyrrolidone. Examples of suitable polymers that are at least weakly hydrophobic include such as, poly (caprolactone), poly(L-lactic acid), poly (glycolic acid), similar co-polymers of theses acids. The present invention provides a method of depositing fibers on a surface, for example to form a dressing for a surface area of an animal for example an area of skin, a wound or burn or for other therapeutic or cosmetic reasons, which comprises using the mixture 5 with a biocompatible polymer which may be bioabsorbable or biodegradable polymer such as polylactic acid, polygylcolic acid, polyvinyl alcohol or polyhydroxybutyric acid. The ratio of polymer to solvent in the mixture 5 may vary from between about 90:10 to about 30:70. In one embodiment, the electroconductivity of the mixture 5 ranges from about $10^4$ to about $10^{10}$ Ohm/cm.

Other additives, either soluble or insoluble, may also be incorporated into the fibers. Preferably, these additives are medically important topical additives provided in at least therapeutic effective amounts for the treatment of the patient or for a skin treatment or protection. Such amounts depend greatly on the type of additive and the physical characteristics of the wound as well as the patient. Examples of such therapeutic additives include, but are not limited to, antimicrobial additives such as silver-containing agents, iodine, and antimicrobial polypeptides, analgesics such as lidocaine, soluble or insoluble antibiotics such as neomycin, thrombogenic compounds, nitric oxide releasing compounds such as sydnonimines and NO-complexes that promote wound healing, other antibiotic compounds, bactericidal or bacteriostatic compounds, fungicidal compounds, analgesic compounds, other pharmaceutical compounds, fragrances, odor absorbing compounds, and nucleic acids. Other additives may include vitamins, antioxidants, insect and animal repellent, dye, V, visible and infrared absorbing or reflecting additives, cosmetic additives, paints for fiber coloring, adhesives, hair treatment, removal, extension, volumizing, protection, coloring, restoration additives, tattoo and skin defect covering, discoloration removal, and skin juvenilation additives.

EXAMPLE

The device shown in FIG. 7 was for application of a microfiber coating 1 on human skin. The mixture 5 included polyvinilpirralidone (M=360,000) and poly-d,l-lactide (M=150,000), in ratio 1:10, and 80% of solvent ethyl acetate. The flow rate of the mixture 5 was 1 mL/min, the flow rate of the compressor 8 was 30 l/min, the flow rate of the additional air flow with controlled relative humidity of about 10% was 6 l/min. The electrical field strength between the capillary 6 and the surface 2 was 1.5 kV/cm. The distance between the outlet 10 and the surface 2 was 1 cm. The size of the microfibers was about 0.2 microns. The thickness of the microfiber coating 1 was 1 mm. Emission of solvent vapors was insignificant.

A method and device embodying the invention may also be used for non-medical or skin treatment purposes. For example, coatings of fibers, particles or microcapsules may be formed on substrates such as paper with good control of the thickness and uniformity of the coating. For example, an adhesive may be deposited onto a substrate using the apparatus and method of the present invention.

Materials formed of two or more components which have only a short-shelf life when mixed together may be formed in a timely manner by encapsulating the respective components in respective fibers, particles, or microcapsules so that mixing of the various components only occurs when the components are released from the encapsulating material by, for example, leaching through the encapsulating material, rupture from pressure applied to the encapsulating material, temperature, or degradation, for example bioabsorption or biodegradation, of the encapsulant. Such a method may be used to form, for example, two component adhesives which may be applied separately or simultaneously to a surface as fibers, particles or microcapsules.

Although the present invention has been described with reference to exemplary embodiments, persons skilled in the art will recognize that changes may be made in form and detail without departing from the spirit and scope of the invention. In particular, the coatings produced according to the present-invention are not necessarily limited to those achieved using the apparatus described. Thus, the scope of the invention shall include all modifications and variations that may fall within the scope of the claims.

I claim:

1. An apparatus for forming a microfiber coating on a surface, the apparatus comprising:

a housing including a substantially cylindrical outer tube defining at least one internal volume, the tube having a first end and an outlet at a second end;

a cartridge of a fiber-forming mixture coupled to the housing near the first end of the outer tube for introducing the fiber-forming mixture into the internal volume;

a power source coupled to the housing to generate an electric field between the cartridge and the outlet for enhancing travel of the fiber-forming material from the cartridge to the outlet;

a compressed gas source having an inlet coupled to the housing near the second end for introducing a gas into the internal volume; and at least one additional outlet in the housing near the first end for facilitating flow of the gas from the inlet toward the first end.

2. The apparatus of claim 1 wherein the inlet is configured to create a vortex of the gas around the fiber-forming material.

3. The apparatus of claim 1 wherein the inlet extends through the outer tube.

4. The apparatus of claim 1 wherein the outer tube is made from a non-electrically conductive material.

5. The apparatus of claim 1 wherein the compressed gas source is a micro compressor.

6. The apparatus of claim 1 further including a preconditioned gas source coupled to the first end of the outer tube, the preconditioned gas source adapted to provide a preconditioned gas to the internal volume.

7. The apparatus of claim 1 further comprising a second tube disposed inside and substantially coaxial to the outer tube, wherein a space between the outer tube and the second tube is closed at the first end and open at the second end.

8. The apparatus of claim 7 wherein the at least one additional outlet near the first end is connected to a preconditioned gas source having a first pressure greater than a second pressure inside the second tube.

9. The apparatus of claim 7 wherein the second tube is shorter than the outer tube.

10. The apparatus of claim 7 wherein the second tube includes openings capable of allowing gas exchange between the space and an internal volume of the second tube.

11. The apparatus of claim 1 wherein the diameter of the outer tube is smaller at the second end than at the first end.

12. The apparatus of claim 1 further comprising an electrode located near the second end of the outer tube and defining a plurality of openings to keep the second end of the outer tube substantially open.

13. The apparatus of claim 1 further comprising a distance sensor for measuring a distance between a point on the housing and the surface.

14. The apparatus of claim 13 further comprising a control circuit for adjusting a voltage of the power source in response to a signal from the distance sensor.

15. The apparatus of claim 1 further comprising a gas conditioner fluidly coupled to the additional outlet for receiving at least some of the gas introduced into the volume by the compressed gas source.

16. An apparatus for forming a microfiber coating on a surface, the apparatus comprising a housing provided with an internal space and an opening, the housing having a port communicating with the internal space, a supply of a fiber-forming liquid coupled to the port for introducing the fiber-forming liquid into the internal space, a voltage source coupled to the housing for creating an electrical potential between the port and the surface so as to cause the fiber-forming liquid to travel from the port to the opening in a stream having a periphery and means including at least one inlet near the opening in the housing and at least one outlet near the supply for reducing an ambient pressure around the periphery of the stream so as to remove moisture from the stream.

17. The apparatus of claim 16 wherein said means includes a compressed gas source coupled to the inlet to inject gas into the internal space and thus reduce the ambient pressure around the periphery of the stream.

18. The apparatus of claim 17 wherein the compressed gas source is coupled to the at least one outlet to draw the gas out of the internal space.

19. The apparatus of claim 17 wherein the at least one inlet is configured to create a vortex of the gas around the fiber-forming liquid.

20. An apparatus for forming a microfiber coating on a surface, the apparatus comprising:

a housing including a substantially cylindrical outer tube defining at least one internal volume, the tube having a first end and an outlet at a second end;

a cartridge of a fiber-forming liquid solution, the cartridge coupled to the housing near the first end of the outer tube for introducing the fiber-forming liquid solution into the at least one internal volume;

a power source coupled to the housing to generate an electric field between the cartridge and the outlet for enhancing travel of the fiber-forming material from the cartridge to the outlet; and a compressed gas source having an inlet extending through the outer tube for introducing a gas into the at least one internal volume.

21. The apparatus of claim 20 wherein the inlet is configured to create a vortex of the gas around the fiber-forming liquid solution.

22. The apparatus of claim 20 wherein the diameter of the outer tube is smaller at the second end than at the first end.

23. The apparatus of claim 20 further comprising a gas conditioner coupled to an additional outlet in the housing near the first end for conditioning the gas introduced into the at least one internal volume by the compressed gas source.

24. The apparatus of claim 20 further comprising an inner tube disposed inside and substantially coaxial to the outer tube, wherein a space between the outer tube and the inner tube is closed at the first end and open at the second end.

25. The apparatus of claim 24 wherein the compressed gas source has a first pressure greater than a second pressure inside the inner tube.

26. The apparatus of claim 24 wherein the inner tube is shorter than the outer tube.

27. The apparatus of claim 24 wherein the inner tube includes openings capable of allowing gas exchange between the space and an internal volume of the inner tube.

* * * * *